United States Patent [19]

Piantadosi et al.

[11] Patent Number: 5,282,467
[45] Date of Patent: Feb. 1, 1994

[54] NON-INVASIVE METHOD FOR DETECTING DEEP VENOUS THROMBOSIS IN THE HUMAN BODY

[75] Inventors: Claude A. Piantadosi; Benjamin J. Comfort, both of Durham, N.C.; Neil B. Hampson, Seattle, Wash.

[73] Assignee: Duke University, Durham, N.C.

[21] Appl. No.: 930,002

[22] Filed: Aug. 13, 1992

[51] Int. Cl.$^5$ ............................................. A61B 5/00
[52] U.S. Cl. .................... 128/633; 128/666; 356/41
[58] Field of Search .............. 128/672, 633, 664, 665, 128/677, 666, 667; 356/39–41

[56] References Cited

U.S. PATENT DOCUMENTS

| | | | |
|---|---|---|---|
| 4,015,595 | 4/1977 | Benjamin, Jr. | 128/2.05 V |
| 4,030,485 | 6/1977 | Warner | 128/2.05 A |
| 4,223,680 | 9/1980 | Jöbsis | 128/633 |
| 4,281,645 | 8/1981 | Jöbsis | 128/633 |
| 4,321,930 | 3/1982 | Jöbsis et al. | 128/633 |
| 4,380,240 | 4/1983 | Jöbsis et al. | 128/633 |
| 4,432,374 | 2/1984 | Osanai | 128/694 |
| 4,463,762 | 8/1984 | Rubens | 128/633 |
| 4,494,550 | 1/1985 | Blazek et al. | 128/664 |
| 4,510,938 | 4/1985 | Jöbsis et al. | 128/633 |
| 4,597,393 | 7/1986 | Yamakoshi et al. | 128/677 |
| 4,726,382 | 2/1988 | Boehmer et al. | 128/667 |
| 4,730,621 | 3/1988 | Stott | 128/667 |
| 4,883,055 | 11/1989 | Merrick | 128/633 |
| 5,099,853 | 3/1992 | Uemura et al. | 128/679 |
| 5,152,297 | 10/1992 | Meister et al. | 128/672 |

OTHER PUBLICATIONS

Hampson and Piantadosi, "Near Infrared Monitoring of Human Skeletal Muscle Oxygenation During Forearm Ischemia", *American Physiological Society*, Jun. 1988, pp. 1–9.

Mitrani, et al., "Detection of Clinically Suspected Deep Vein Thrombosis Using Light Reflection Rheography", *The American Journal of Surgery*, vol. 161, Jun. 1991, pp. 646–650.

Mukherjee, et al., "Use of Light Reflection Rheography for Diagnosis of Axillary or Subclavian Venous Thrombosis", *The American Journal of Surgery*, vol. 161, Jun. 1991, pp. 651–656.

*Primary Examiner*—Angela D. Sykes
*Attorney, Agent, or Firm*—Richard E. Jenkins

[57] ABSTRACT

A non-invasive method for detecting deep venous thrombosis in a human body wherein changes are effected in the amount of deoxyhemoglobin in the body limb by trapping blood in the venous system for a determinate time period and then releasing the trapped blood in the venous system. During the period that the changes in the amount of deoxyhemoglobin are effected, first and second light sources emit light of two selected wavelengths which penetrate into the deep venous system of the body limb so that the reflectance contributions can be used to measure changes in the flow and amount of deoxyhemoglobin and to thereby detect the presence or absence of deep venous thrombosis.

14 Claims, 2 Drawing Sheets

NON-INVASIVE METHOD FOR DETECTING DEEP VENOUS THROMBOSIS IN THE HUMAN BODY

TECHNICAL FIELD

The present invention relates to a method for non-invasively detecting deep venous thrombosis. More specifically, the present invention relates to a non-invasive method for measuring deep venous thrombosis by measuring the rate of change and amount of change in venous blood volume which is restricted and then released in accordance with the process. of the invention.

RELATED ART

Venous insufficiency of the extremities is a result of diseases in the venous circulation which lead to impaired drainage of the venous vessels into the central veins of the body. The most common and important clinical problem associated with impaired venous drainage of the extremities is deep venous thrombosis. Deep venous thrombosis is determined by the presence of acute or chronic blood clots in the veins of an extremity which results in impaired flow of blood out of the venous system. The presence of deep venous thrombosis is a clinical problem because of the local consequences of the clot, i.e., swelling and inflammation, as well as the possibility that the clot will break free from the vein and migrate through the venous circulation and heart and become lodged in the lungs. This process is called pulmonary embolization.

A number of methods are available to evaluate peripheral venous disorders including deep venous thrombosis. These methods include the following well-known procedures:
1. Volume measurement (plethysmography) using either a strain gauge or impedance techniques;
2. Venous pressure measurement (phlebodynamometry);
3. Phlebography using radio contrast;
4. Radio-labeled fibrinogen nuclear medicine scans;
5. Thermography;
6. Light reflectance rheography (LRR);
7. Magnetic resonance imaging (MRI); and
8. Ultrasound.

All of these techniques are non-invasive except for phlebography and the radio-labeled fibrinogen scan which both require injections of tracer material into the circulation. This tracer is a radiocontrast dye in the former case and radioactive albumin in the latter. Both techniques are relatively expensive. The other referenced techniques are non-invasive but all have their own relative shortcomings.

For example, both plethysmography and thermography techniques possess problems with respect to sensitivity and specificity. Plethysmography is a non-invasive technique for evaluating venous insufficiency by detecting changes in the blood volume in a whole segment of an extremity including skin, subcutaneous tissue, muscle and bone. This may be done using a strain gauge, an impedance device or with a water-filled or gas-filled plethysmograph. Changes in volume in the area of measurement produce changes in circumference on the surface and volume changes are inferred from the circumference changes. Thermography is a non-invasive technique for assessing changes in temperature due to changes in blood flow which is accomplished using an infrared camera.

Light reflectance rheography (LRR) measures changes in light reflectance from the skin which are related to changes in geometry of the blood vessels in proportion to changes in pressure in the microcirculation of the skin. Since this signal is derived from the skin, it may or may not reflect changes in the amount of blood present in the deep venous system below the skin. Phlebodynamometry is a technique for measuring venous pressure changes which is accomplished by use of pressure sensitive transducers.

All of the above-noted techniques have problems due to lack of accuracy of measurement, lack of reproducibility and technical complexity in performing the measurements.

Ultrasonic techniques based on the Doppler effect have also been used as a non-invasive qualitative method for evaluating venous circulation by recording blood velocity. These techniques, however, are not particularly quantitative. Finally, magnetic resonance imaging (MRI) has been used, but this requires placing either the entire patient or the patient's limb to be studied in a powerful magnetic field. This is inconvenient, requires movement of the patient into the magnet and is quite an expensive procedure.

The above-referenced technique which could be the most pertinent to applicants' process is the light reflection rheography (LRR). Light reflection rheography is based on optical scanning of pressure changes in the cutaneous capillary bed to diagnose deep venous thrombosis. The technique tests for pressure changes in the cutaneous capillary bed in response to exercise which are believed to be a reflection of the status of the superficial and deep venous system in the absence of advanced arterial insufficiency. Representative LRR instrumentation includes a sensor which is secured to the limb being investigated and formed with a plurality of light-emitting diodes providing an emission near the infrared range of the light spectrum (to prevent interference by other light sources) and a photodetector adjacent thereto. The sensor is electrically connected to an electronic measuring evaluation unit and a recorder. In use, venous outflow from a limb is tested by applying venous congesting pressure by changes in position or inflation of a blood pressure cuff and measuring the rate of venous outflow when the congesting pressure is released. Rapid release of the congesting pressure provided by the pressure cuff leads to venous emptying which can be memorialized in a recorder tracing. As is well known to those familiar with LRR, failure to demonstrate venous emptying by this maneuver is probably to date the single most reliable indication of deep venous occlusion in a limb.

DISCLOSURE OF THE INVENTION

In accordance with the present invention, applicants provide a non-invasive method for detecting deep venous thrombosis in a human body comprising first securing an inflatable cuff to a body limb of interest wherein the body limb comprises skin, bare and soft tissues, and blood vessels containing oxyhemoglobin and deoxyhemoglobin. Next, radiation source means and associated photodetector means are attached to the body limb proximate to the inflatable cuff, and the radiation source means is actuated s that radiation penetrates through the skin and to the deep venous system of the body limb. Changes are then effected in the amount of deoxyhemoglobin in the body limb by inflating the cuff during the actuation of the radiation source means to a pressure below arterial pressure so as to trap blood in the venous system for a determinate time period and then by deflating the cuff during the radiation source means actuation.

The effected changes are detected by actuating the photodetector means associated with the radiation source means to detect changes occurring during the filling of the venous system after the cuff is inflated and during the emptying of the venous system after the cuff is deflated by measuring reflectance contributions including contributions from the skin, soft tissues, oxyhemoglobin and deoxyhemoglobin in the blood vessels of the body limb. Finally, the presence of deep venous thrombosis is detected by subtracting the reflectance contributions of the skin, tissues and oxyhemoglobin from the reflectance contributions of the deoxyhemoglobin which is contained virtually exclusively in the venous system blood vessels.

It is therefore the object of the present invention to provide a method for non-invasively detecting the presence of deep venous thrombosis in a human body limb.

It is another object of the present invention to non-invasively detect deep venous thrombosis by measuring changes in venous blood volume and the rate of change in blood volume (flow) occurring during restriction and release of the venous blood flow by means of two light sources of different wavelengths such that spectral absorbance of hemoglobin in its deoxygenated form as found in the deep venous system can be measured.

It is still another object of the present invention to provide a more accurate process for measuring deep venous thrombosis than that provided by conventional light reflection rheography (LRR).

DESCRIPTION OF THE DRAWINGS

Some of the objects of the invention having been stated, other objects will become evident as the description proceeds, when taken in connection with accompanying drawings, in which.

BEST MODE FOR CARRYING OUT THE INVENTION

Figure 1:
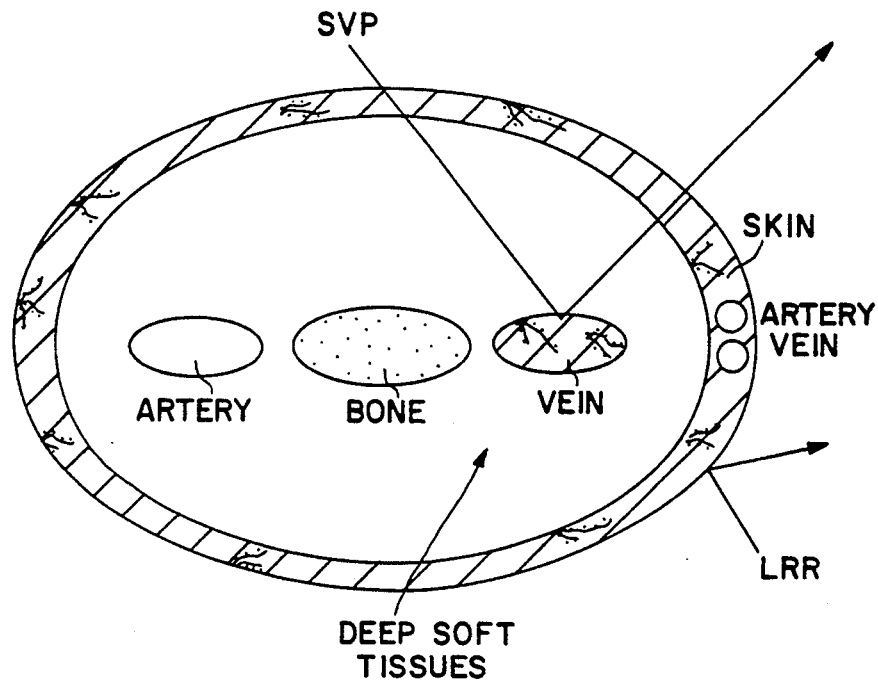
FIG. 1 is a schematic drawing of limb tissues illustrating the location of venous circulation which is obstructed if impaired by deep venous thrombosis.

Applicants' novel spectroscopic venous plethysmography method (SVP) uses a source of radiation which penetrates into the deep tissues of the limb (see FIG. 1) where the venous circulation is impaired by disease such as blood clots. In the deeper tissues where the larger vessels and clots are located, the blood is contained in arterial vessels, the microcirculation (including capillaries) and the venous circulation. The color of the blood in the arterial circulation and the capillaries is primarily the color of oxyhemoglobin. The color of the blood in the venous circulation is a mixture of oxyhemoglobin and deoxyhemoglobin. Only the deep venous system contains an appreciable amount of deoxyhemoglobin.

SVP measures the amount of deoxyhemoglobin present in a limb and therefore is sensitive only to blood which is contained in the deep venous system. The process relies on a plurality of selected sources of radiation in the red and infrared region of the light spectrum to measure the amount of deoxyhemoglobin present in the optical field. This can be done with as few as two wavelengths as shown in the preferred embodiment described herein or by using as many wavelengths as the entire light spectrum (e.g., white light).

The intensity of the light recovered from the tissues deeper than the skin is detected by a photodetector and analyzed by a computer according to an algorithm which subtracts the reflectance contributions of the skin, the tissues and the oxyhemoglobin from the reflectance contributions of the deoxyhemoglobin. Changes in the amount of deoxyhemoglobin present in the limb are effected by mechanical maneuvers which change the volume of deoxyhemoglobin in the veins. In the preferred embodiment of applicants' inventive process, a blood pressure cuff is used and rapidly inflated to a pressure below arterial pressure to trap blood in the venous system. The changes in the filling of the venous system are recorded and after a new steady state is reached, the pressure on the cuff is released and the characteristics of the emptying of deoxyhemoglobin from the venous system are also recorded.

Figure 2:
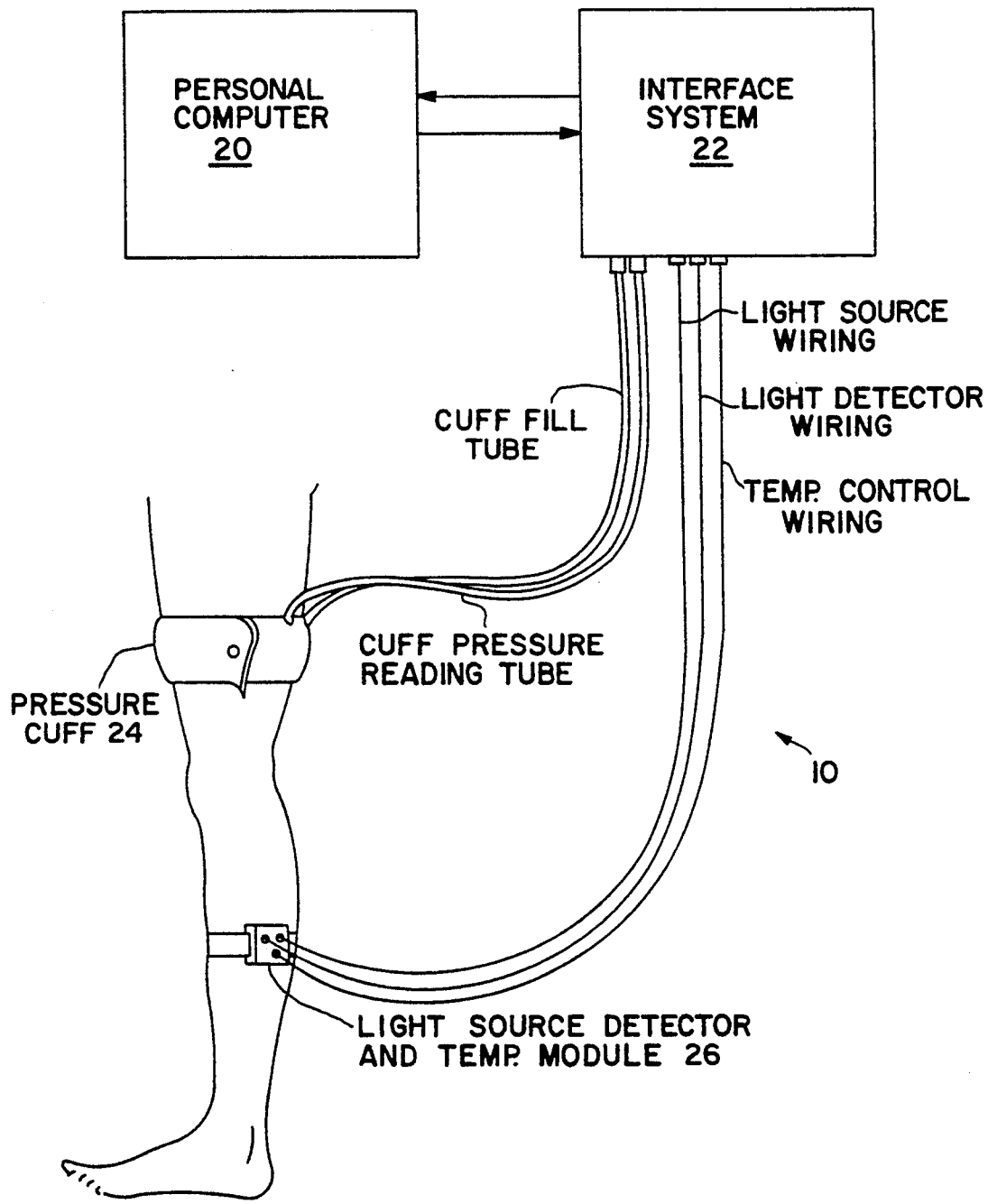
FIG. 2 is a schematic view of a representative apparatus for practicing the method of the present invention.

Referring now to FIG. 2, an apparatus 10 has been constructed by applicants to practice the novel process comprising a personal computer 20 (a 20 megahertz 386 PC), an interface system 22, an inflatable pressure cuff 24 and light module 26 containing two light sources (660 nm LED and 809 nm CW Laser Diode), a photodetector, and a heating element (not shown). Interface system 22 contains drivers for the two light sources, a measuring circuit for the photodetector (a photodiode), a temperature control circuit to maintain the heating element at about 35° C. temperature, and an air pump with a pressure regulator to control the air pressure in blood pressure cuff 24. The computer interface system 22 is connected to blood pressure cuff 24 and module 26 by suitable air tubes and electronic wiring.

In use, pressure cuff 24 is placed and secured above light module 26 on the limb of interest. (Light module 26 is maintained at skin temperature to stabilize the solid state opto-electronic light emittance and detector devices.) Photons are emitted from the two light sources of module 26 into the limb and a fraction of the light from the deep tissues is recovered by the photodetector of module 26. A photosignal is then carried back through interface system 22 and to personal computer 20 where a suitable algorithm is applied to determine the presence of deep venous thrombosis.

Apparatus 10 tracks changes in deoxyhemoglobin using photosignals derived from two or more wavelengths. In the preferred embodiment of the invention, the two measuring wavelengths are 660 nanometers and 809 nanometers, but the effective range for each is believed to be between 600 to 800 and 800 to 1000 nanometers respectively. Changes in the SVP signals are measured from a baseline value by measuring differences in the absorption of light at the two wavelengths relative to incident light reflected from the skin. The incident light signals are initially set at a constant one unit at each of the two wavelengths. Total absorbencies are computed for each wavelength and the values subtracted to provide the relative concentrations of both deoxyhemoglobin and oxyhemoglobin.

The calculations may be done by using a form of the Beer Lambert Law that states that optical density (absorbance) is equal to minus log to the base ten times (IO/I) where IO is the measured or transmitted light and I is the incident light. Since I is constant, IO can be used directly. Thus, the deoxyhemoglobin is equal to minus the log to the base ten at 660 nanometers minus the negative log to the base ten of 809 nanometers. The 660 nanometers contains absorption primarily due to deoxyhemoglobin and the skin and tissue while 809 nanometers is an isosbestic point for oxy- and deoxyhemoglobin. It also contains the same contribution from the skin and soft tissues. Thus, the deoxyhemoglobin value is equal to minus the log to the base ten of 660 plus log to the base ten of 809, or log to the base ten of 809 minus log to the base ten of 660. Of course, other algorithms can be used to isolate and measure the contribution of deoxyhemoglobin to the measurements of reflected light and thereby to detect the presence of deep venous thrombosis.

Figure 3:
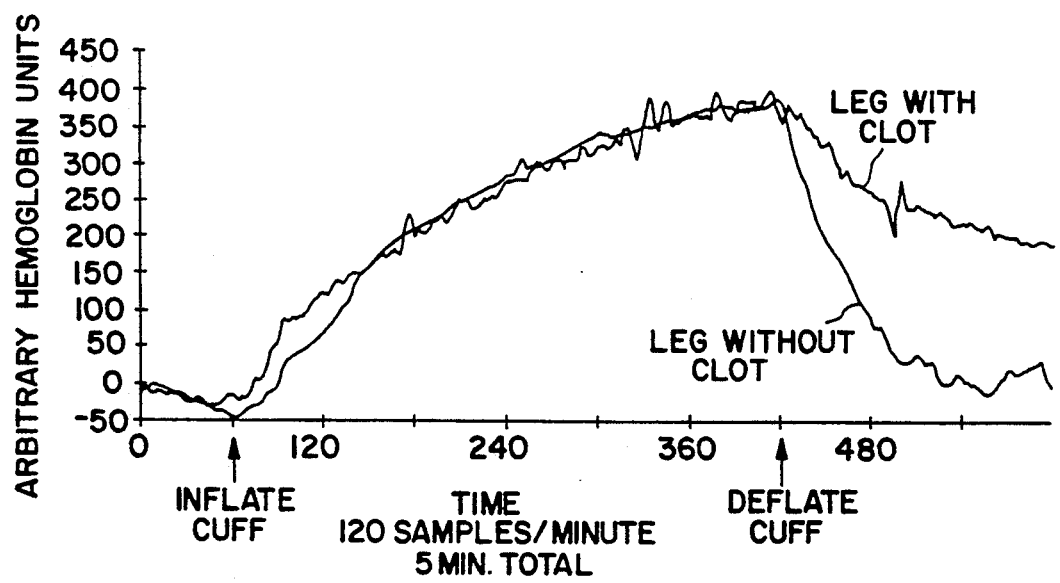
FIG. 3 is a graph illustrating signals obtained from a healthy limb versus a diseased limb practicing the method of the present invention.

FIG. 3 is a graph illustrating signals obtained from a healthy limb versus from a diseased limb using applicants' novel methodology.

For a still better understanding of applicants' invention, a description is set forth below in Table 1 of representative test equipment for practicing the novel diagnostic method of applicants, invention for detecting the presence of deep venous thrombosis in a body limb.

TABLE 1

Applicants' Test Equipment
    Interface system designed and built by the inventors
        Personal Computer (80386-20) from Tangent, Inc.
        National Instruments AT-M10-16 Data Acquisition
    Adapter Board
    Light Source 1 Wavelength: 660 nm LED
    Light Source 2 Wavelength: 809 nm Continuous Wave
        (CW) Laser Diode It will be understood that the various details of this invention may be changed without departing from the scope of the invention. Furthermore, the foregoing description is for the purpose of illustration only, and not for the purpose of limitation—the invention being defined by the claims.

What is claimed is:

1. A non-invasive method for detecting deep venous thrombosis in a human body, said method comprising the steps of:

(a) securing an inflatable cuff to a body limb of interest wherein said body limb comprises skin, tissues, oxyhemoglobin and deoxyhemoglobin;

(b) attaching a radiation source and operatively associated photodetector to the body limb proximate to said inflatable cuff;

(c) actuating said radiation source so that radiation penetrates through the skin and into the deep venous system of the body limb to enable detecting of changes in the amount of deoxyhemoglobin in said deep venous system;

(d) effecting changes in the amount of deoxyhemoglobin in the body limb by inflating said cuff during said radiation source actuation to a pressure below arterial pressure to trap blood in the venous system for a determining a time period and by deflating said cuff during said same radiation source actuation;

(e) actuating said photodetector to detect changes occurring during the trapping of the blood in the venous system after said cuff is inflated and during the emptying of the venous system after said cuff is deflated by measuring reflectance contributions including contribution from the skin, tissues, oxyhemoglobin and deoxyhemoglobin of the body limb; and (f) detecting the presence of deep venous thrombosis by subtracting the reflectance contributions of the skin, tissues and oxyhemoglobin from the reflectance contribution of the deoxyhemoglobin and comparing the reflectance contribution of the deoxyhemoglobin to predetermined reflectance values for a normal body limb.

2. A non-invasive method for detecting deep venous thrombosis according to claim 1 wherein said radiation source comprises at least two light sources.

3. A method according to claim 2 wherein said at least two light sources comprise two light sources wherein said emitted light from said first light source has a wavelength between about 600 to 800 nanometers and emitted light from said second light source has a wavelength between a bout 800 to 1000 nanometers.

4. A method according to claim 2 wherein said at least two light sources comprise at least one light-emitting diode (LED).

5. A method according to claim 1 wherein said inflatable cuff and said radiation source and operatively associated photodetector are electrically connected to and controlled by a computer.

6. A method according to claim 5 wherein said deep venous thrombosis detecting step is calculated by said computer.

7. A non-invasive method for detecting deep venous thrombosis in a human body, said method comprising the steps of:

(a) securing an inflatable cuff to a body limb of interest wherein said body limb comprises skin, tissues, oxyhemoglobin and deoxyhemoglobin;

(b) attaching first and second light sources and an operatively associated photodetector to the body limb proximate to said inflatable cuff, said first light source emitting light having a wavelength between about 600 to 800 nanometers and said second light source emitting light having a wavelength between about 800 to 1000 nanometers;

(c) actuating said first and second light sources so that light emitted therefrom penetrates through the skin and into the deep venous system of the body limb to enable detecting of changes in the amount of deoxyhemoglobin in said deep venous system;

(d) effecting changes in the amount of deoxyhemoglobin in the body limb by inflating said cuff during said light source actuation to a pressure below arterial pressure to trap blood in the venous system for a determinate time period and by deflating said cuff during said same light source actuation to release blood from the venous system;

(e) actuating said photodetector to detect changes occurring during the trapping of the blood in the venous system after said cuff is inflated and during the emptying of the venous system after said cuff is deflated by measuring light reflectance contributions from said first and second light sources including contributions from the skin, tissues, oxyhemoglobin and deoxyhemoglobin of the body limb; and (f) detecting the presence of deep venous thrombosis by subtracting the reflectance contributions of the skin, tissues and oxyhemoglobin from the reflectance contribution of the deoxyhemoglobin and comparing the reflectance contribution of the deoxyhemoglobin to predetermined reflectance values for a normal body limb.

8. A method according to claim 7 wherein said light sources comprise one light-emitting diode (LED) and one continuous wave (CW) laser diode.

9. A method according to claim 7 wherein said emitted light from said first light source is absorbed primarily by said deoxyhemoglobin, skin and tissues and said emitted light from said second light source is absorbed primarily by said oxyhemoglobin, deoxyhemoglobin, skin and tissue.

10. A method according to claim 7 wherein said inflatable cuff and said first and second light sources and operatively connected photodetector are electrically connected to and controlled by a computer.

11. A method according to claim 10 wherein said deep venous thrombosis detecting step is calculated by said computer.

12. A method according to claim 10 wherein said computer comprises an electronic computer and interface system.

13. A non-invasive method for detecting deep venous thrombosis in a human body, said method comprising the steps of:

(a) securing an inflatable cuff to a leg wherein said leg comprises skin, tissues, oxyhemoglobin and deoxyhemoglobin;

(b) attaching a radiation source and operatively associated photodetector to the leg proximate to said inflatable cuff;

(c) actuating said radiation source sot hat radiation penetrates through the skin and into the deep venous system of the leg to enable detecting of changes in the amount of deoxyhemoglobin in said deep venous system;

(d) effecting changes in the amount of deoxyhemoglobin in the leg by inflating said cuff during said radiation source actuation to a pressure below arterial pressure to trap blood in the venous system for a determinate time period and by deflating said cuff during said same radiation source actuation to release blood from the venous system;

(e) actuating said photodetector to detect changes occurring during the trapping of the blood in the venous system after said cuff is inflated and during the emptying of the venous system after said cuff is deflated by measuring reflectance contributions including contributions from the skin, tissues, oxyhemoglobin and deoxyhemoglobin of the leg; and (f) detecting the presence of deep venous thrombosis by subtracting the reflectance contributions of the skin, tissues and oxyhemoglobin from the reflectance contribution of the deoxyhemoglobin and comparing the reflectance contribution of the deoxyhemoglobin to predetermined reflectance values for a normal leg.

14. A non-invasive method for detecting deep venous thrombosis in a human body, said method comprising the steps of:

(a) securing an inflatable cuff to a leg wherein said leg comprises skin, tissues, oxyhemoglobin and deoxyhemoglobin;

(b) attaching first and second light sources and an operatively associated photodetector to the leg proximate to said inflatable cuff, said first light source emitting light having a wavelength between about 600 to 800 nanometers and said second light source emitting light having a wavelength between about 800 to 1000 nanometers;

(c) actuating said first and second light sources so that light emitted therefrom penetrates through the skin and into the deep venous system of the leg to enable detecting of changes int he amount of deoxyhemoglobin in said deep venous system;

(d) effecting changes int he amount of deoxyhemoglobin in the leg by inflating said cuff during said light source actuation to a pressure below arterial pressure to trap blood in the venous system for a determinate time period and by deflating said cuff during said same light source actuation to release blood from the venous system;

(e) actuating said photodetector to detect changes occurring during the trapping of the blood int eh venous system after said cuff is inflated and during the emptying of the venous system after said cuff is deflated by measuring light reflectance contributions from said first and second light sources including contributions from the skin, tissues, oxyhemoglobin and deoxyhemoglobin of the leg; and (f) detecting the presence of deep venous thrombosis by subtracting the reflectance contributions of the skin, tissues and oxyhemoglobin from the reflectance contribution of the deoxyhemoglobin and comparing the reflectance contribution of the deoxyhemoglobin to predetermined reflectance values for a normal leg.

* * * * *